United States Patent [19]
Jacobson et al.

[11] Patent Number: 5,298,508
[45] Date of Patent: Mar. 29, 1994

[54] IRREVERSIBLE INHIBITORS OF ADENOSINE RECEPTORS

[75] Inventors: Kenneth A. Jacobson, Silver Spring, Md.; Gary Stiles, Chapel Hill, N.C.

[73] Assignees: The United States of America as represented by the Department of Health and Human Services, Washington, D.C.; Duke University, Durham, N.C.

[21] Appl. No.: 837,105

[22] Filed: Feb. 18, 1992

Related U.S. Application Data

[63] Continuation of Ser. No. 221,413, Jul. 19, 1988, abandoned.

[51] Int. Cl.$^5$ .................. A61K 31/52; A01N 43/90; C07D 473/06; C07D 473/34
[52] U.S. Cl. .................. 514/263; 514/261; 514/265; 514/266; 544/267; 544/277; 544/269
[58] Field of Search .................. 544/267, 269; 514/263, 514/265

[56] References Cited

U.S. PATENT DOCUMENTS

| 2,840,559 | 6/1958 | Krantz, Jr. et al. | |
| 3,317,533 | 5/1987 | De Ridder. | |
| 3,641,010 | 2/1972 | Schweiss et al. | |
| 4,233,303 | 11/1980 | Bergstrand et al. | 424/253 |
| 4,299,832 | 11/1981 | Brown et al. | 424/253 |
| 4,364,922 | 12/1982 | Berne et al. | 424/9 |
| 4,452,788 | 6/1984 | Bristol | 424/253 |
| 4,456,687 | 6/1984 | Green | 435/241 |
| 4,469,698 | 9/1984 | Philippossian et al. | 424/253 |
| 4,472,572 | 9/1984 | Shizuya | 536/27 |
| 4,546,182 | 10/1985 | Kjellin et al. | 544/273 |
| 4,548,820 | 10/1985 | Regnier et al. | |
| 4,568,676 | 2/1986 | Smith | 514/258 |
| 4,593,095 | 6/1986 | Snyder et al. | 544/272 |
| 4,612,315 | 9/1986 | Jacobson et al. | 514/263 |

Primary Examiner—Mukund J. Shah
Assistant Examiner—Matthew V. Grumbling
Attorney, Agent, or Firm—Leydig, Voit & Mayer

[57] ABSTRACT

Irreversible ligands for adenosine receptors are derived from agonist and antagonist functionalized congeners which contain electrophilic acylating and alkylating groups for reaction at nucleophilic residues of adenosine receptors. The ligands are based on 8-aryl-substituted xanthines as antagonists and on $N^6$-substituted adenosine as agonists, wherein the electrophlic group may be, for example, isothiocyanate and N-hydroxysuccinimide esters.

18 Claims, 2 Drawing Sheets

XAC                    DITC

DITC-XAC

IRREVERSIBLE INHIBITORS OF ADENOSINE RECEPTORS

This application is a continuation of application Ser. No. 07/221,413 filed on Jul. 19, 1988, now abandoned.

FIELD OF THE INVENTION

The present invention relates to improvements in therapy and, more particularly, to irreversible ligands for adenosine receptors based on 8-aryl-substituted xanthines as antagonists or $N^6$-substituted adenosine as agonists.

BACKGROUND OF THE INVENTION

Adenosine acts as a neuromodulator to inhibit neuromal firing and the release of neurotransmitters, as an inhibitor of platelet aggregation, as a cardiac depressant, and as as a vasodilator, a vasoconstrictor, as in the renal afferent arterioles and in the skin, as an immunosuppressant, and in a variety of other systems. Most of the physiological effects of adenosine involve binding to discrete membrane-bound adenosine receptors of the $A_1$ or $A_2$ subtypes. The xanthine drugs caffeine and theophylline, and many synthetic analogs, act as competitive antagonists at adenosine receptors. cf. K. A. Jacobson, in *Receptor Biochemistry and Methodology*, Vol. 11, ed. D. M. F. Cooper and C. Londos, pp. 1–26, 988.

Xanthines are well known drugs which are used clinically as bronchodilators, cardiotonics, diuretics, and central nervous system stimulants. The available evidence indicates that the therapeutic actions of these drugs involves blockade or antagonism of adenosine receptors. However, many of the xanthines, such as theophylline (1,3-dimethylxanthine), have undesirable side effects, such as cardiac stimulation. Some of these side effects may be due to actions at sites other than those of adenosine receptors. However, it is also likely that some side effects are associated with blockade of the adenosine receptors themselves.

Irreversible ligands, i.e. ligands that form a stable covalent bond with a receptor, have been synthesized for a number of receptors, including opiate receptors (Rice et al, *Science*, 220: 314–316 (1983) and Portoghese et al, *Ann. Rev. Pharmacol. Toxicol.* 25: 193–223 (1985), PCP (Rice et al. *FEBS Letters* 181: 318–322, 1985), adrenergic receptors (Pitha et al., *J. Med. Chem.* 30: 612–615, 1987), and benzodiazepine receptors (Newman et al., *J. Med. Chem.* 30:1901 (1987). The utility of chemically irreversible ligands for characterizing receptors in membranes and in physiological systems, and in receptor identification, has been demonstrated. For adenosine receptors, only photoaffinty labels have been described (Stiles, *Trends Pharmacol. Sci.* 7:486–490, 1986; Stiles et al., *Mol. Pharmacol.* 32: 184, 1987).

Kjellin et al, U.S. Pat. No. 4,546,182, disclose 3,8-dialkylxanthines which are substituted at the 8-position by methyl, ethyl, n-propyl, isopropyl, cyclopropyl, n-butyl, isobutyl, tert- butyl, or cyclobutyl.

Brown et al, U.S. Pat. No. 4,299,832, disclose substituted theophylline compounds substituted at the 8-position by alkyl or 1 to 6 carbon atoms, cycloalkyl of 3 to 7 carbon atoms, phenyl, or phenylalkyl of 7 to 10 carbon atoms, each of which may be unsubstituted or substituted by one or more hydroxy groups, alkoxy, or alkylthio groups of 1 to 4 carbon atoms, halogen atoms, cyano groups, nitro groups, carboxy groups, alkoxycarbonyl groups of 2 to 5 carbon atoms, amino groups, alkylamino groups of 1 to 4 carbon atoms, or dialkylamino groups of 2 to 8 carbon atoms.

Bergstrand et al, U.S. Pat. No. 4,233,303, disclose xanthine derivatives substituted at the 8-position by methyl or n-propyl.

Bristol, U.S. Pat. No. 4,452,788, discloses 8-phenylxanthines of the following formula:

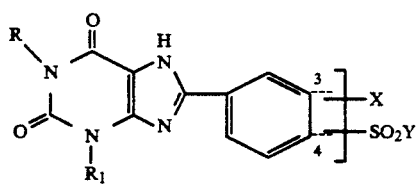

wherein R and $R_1$ may be the same or different and are hydrogen, alkyl of from one to six carbon atoms, $(CH_2)_{2-4}$-$N(R_3)_2$ wherein $R_3$ is alkyl of from one to six carbon atoms, $Ph(CH_2)_{1-3}$, or $CF_3(CH_2)_{1-4}$.

Philippossian et al, U.S. Pat. No. 4,469,698, disclose xanthines substituted in the 8-position by methyl or ethyl.

Snyder et al, U.S. Pat. No. 4,593,095, disclose 8-phenyl-xanthines which are adenosine receptor antagonists. These compounds are of the formula

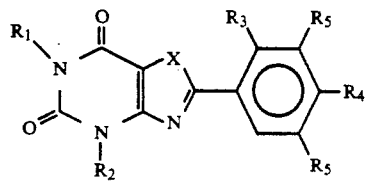

wherein X is NH, O, or S;

$R_1$ is allyl, lower alkyl or cycloalkyl, the lower alkyl or cycloalkyl being substituted with hydroxy, lower alkoxy, or cyano;

$R_2$ is hydrogen, allyl, lower alkyl, or cycloalkyl;

$R_3$ is $NH_2$ or OH;

$R_4$ is halogen, halo-lower alkyl, phenyl, amino, hydroxyl, carboxy, lower alkyl, cycloalkyl, lower alkoxy, cycloalkoxy, lower alkoxyamino, lower alkylamino or cycloalkylamino, optionally substituted with hydroxy, primary amino, secondary amino tertiary amino, or carboxy, provided that $R_3$ and $R_4$ are not both amino when $R_1$ and $R_2$ are both bethyl; and $R_5$, which may be the same or different, is hydrogen, lower alkyl, lower alkoxy, halogen, hydroxyl, nitro, or amino; or X, $R_1$, $R_2$, and $R_5$ have the meaning stated above, $R_3$ is hydrogen, and $R_4$ is hydrogen or has the meaning given above, except that $R_1$ is other than methyl or ethyl when $R_4$ is hydrogen, halogen, $C_1$–$C_3$ alkoxy, amino, or alkylamino and $R_5$ is halogen or hydrogen.

Jacobson et al, U.S. Pat. No. 4,612,315, disclose functionalized congeners of 1,3-dialkylxanthine which are antagonists for $A_1$- and $A_2$- adenosine receptors.

SUMMARY OF THE INVENTION

It is an object of the present invention to overcome disadvantages in the prior art, such as noted above.

It is another object of the present invention to provide functionalized congeners which contain electrophilic acylating and alkylating groups for reaction at nucleophilic residues of adenosine receptors.

It is yet another object of the present invention to provide irreversible ligands for adenosine receptors based on 8-aryl-substituted xanthines as antagonists.

It is a further object of the present invention to provide irreversible ligands for adenosine receptors based on $N^6$-substituted adenosine as agonists.

It is still another object of the present invention to provide for improved diuretics and kidney-protective agents.

It is still a further object of the present invention to provide for improved cardiotonic agents.

It is yet a further object of the present invention to provide for improved stimulators of the immune system.

It is still a further object of the present invention to provide adenosine agonists which are useful as vasodilators, anti-diuretic agents, or immunosuppressants.

According to the present invention, a variety of potentially irreversible ligands for adenosine receptors are provided based on 8-aryl-substituted xanthines as antagonists and on $N^6$-substituted adenosine as agonists. The ligands contain electrophilic groups such as isothiocyanate, bromoacetyl, both of which are reactive either with amines or thiols; pyridyl disulfide and maleimide, which are reactive with thiols; N-hydroxysuccinimide esters and carbonyl functionality, both of which are reactive with amines.

The ligands according to the present invention can comprise adenosine having a spacer chain at the $N^6$-position with an isothiocyanate group at the end of the spacer chain, or xanthine having a spacer chain at the 8-position, with an isothiocyanate group at the end of the spacer chain.

The spacer chain may be any inert chain of atoms separating the xanthine or adenosine from the isothiocyanate group. The spacer chain may consist of $C_2$–$C_{10}$ alkyl or alkylene groups, amide bonds, phenyl rings, thiourea linkages, ether linkages, esters, disulfides, alcohols, halogens including fluorine, chlorine, bromine, and iodine, and various combinations thereof.

DETAILED DESCRIPTION OF THE INVENTION

Figure 1:
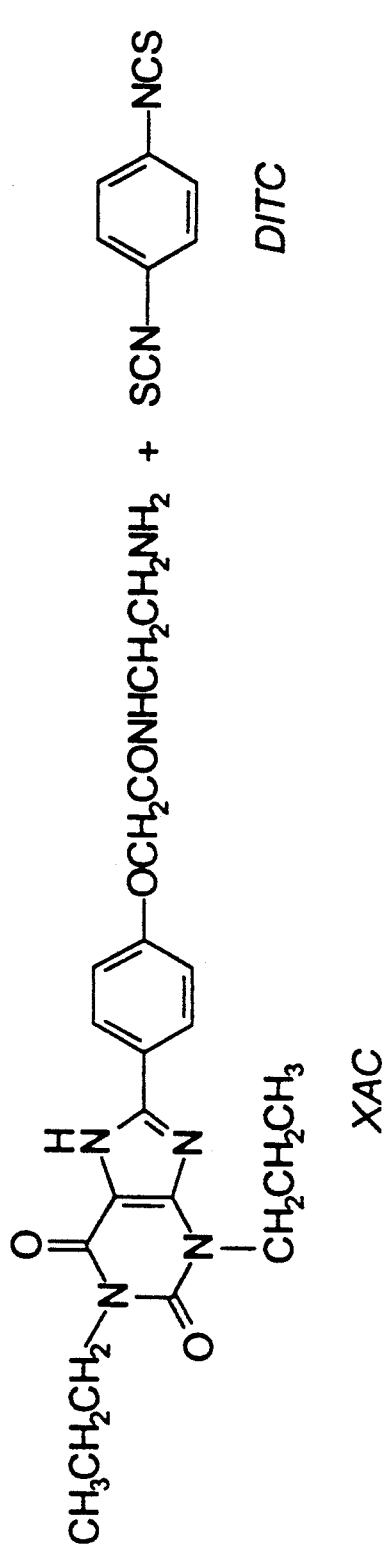
FIG. 1 shows a method of synthesizing an irreversible inhibitor of $A_1$-adenosine receptors.
Figure 1:
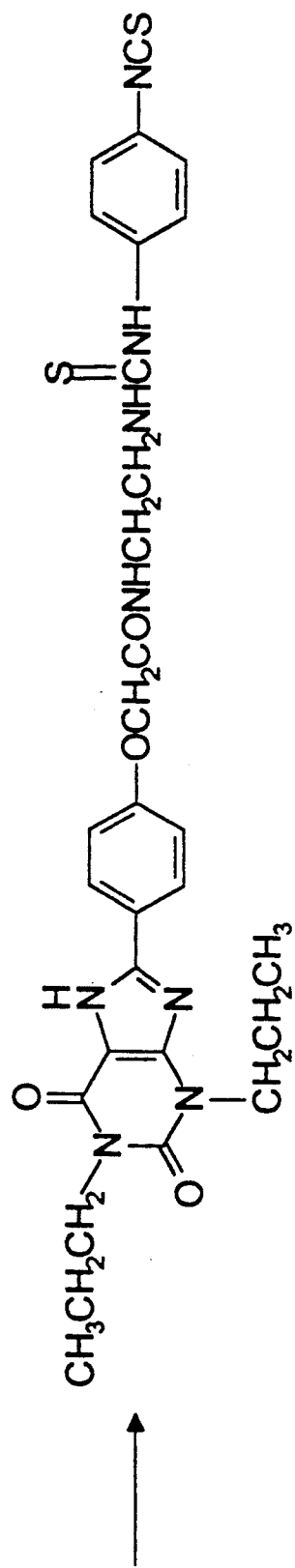

Specific compounds according to the invention based on 8-aryl-substituted xanthines are shown in Table I.

TABLE I

Xanthine Derivatives

Structure: [8-aryl xanthine with $CH_3(CH_2)_2$ and $(CH_2)_2CH_3$ on N1 and N3; 8-position aryl bearing $-OCH_2COR$]

| Compound | | | Ki at central A1 receptors (nM) | | |
|---|---|---|---|---|---|
| | | | rat[a] | calf[b] | % inhib(conc)[c] |
| 1. | R = $-O-N$(COCH$_2$)(COCH$_2$) (phthalimide-type) | | 9.0 ± 0.7 | — | 0(500) |
| 2b. | R = $-NHCH_2CHO$ | | 266 ± 40 | 1.5 ± 0.1 | 0(500) |
| 3.[d] | R = $-NH(CH_2)_2NHR'$; R' = $-H$ | | 1.1 ± 0.05 | 0.2 | — |
| | R' = $-CSNH-$C$_6$H$_4$–X | | | | |
| 4b. | X = 4-NCS | | 6.60 ± 1.31 | 1 | 63(100) |
| 5b. | X = 3-NCS | | 2.39 ± 0.35 | 0.5 | 49(5) |
| 6. | X = 4-CH$_3$ | | 16.0 ± 2.9 | — | — |
| 7. | X = 4-OCH$_3$ | | 20 | — | — |
| 8. | X = 4-F | | 12.8 | — | — |
| 9. | X = 2,3,4,5,6-F$_5$ | | 9.07 ± 0.90 | — | — |
| 10. | X = 4-Br | | 7.26 ± 0.90 | — | — |
| 11. | X = 4-NO$_2$ | | 5 | — | — |
| 12. | X = 4-SO$_3$Na | | 430 | — | — |
| 13. | R' = SO$_2$–C$_6$H$_4$(SO$_2$Cl) | | 2.5 ± 0.47 | — | 20(100) |

TABLE I-continued
Xanthine Derivatives

Structure: 1,3-dipropylxanthine with 8-[4-(OCH₂COR')phenyl] substituent (propyl groups CH₃(CH₂)₂– at N1 and –(CH₂)₂CH₃ at N3).

| Compound | R' | Ki at central A1 receptors (nM) rat[a] | calf[b] | % inhib(conc)[c] |
|---|---|---|---|---|
| 14. | R' = SO₂–C₆H₄–CH₃ | 72 ± 7.2 | — | — |
| 15d. | R' = COCH₂–C₆H₄–NH₂·CF₃COOH | 40 | — | — |
| 15c. | R' = COCH₂–C₆H₄–NHCOOC(CH₃)₃ | 53 ± 12 | — | — |
| 15e. | R' = COCH₂–C₆H₄–NHCSNH–C₆H₄–NCS | 30 | — | 10(100) |
| 16c. | R' = COCH₂NHCSNH–C₆H₄–NCS | 6.85 ± 1.14 | — | 50(500) |
| 17. | R' = CO(CH₂)₄COCH₃ | 44 ± 9 | 3.2 | 0(500) |
| 18. | R' = COCH₂Br | 17.6 ± 1.5 | — | — |
| 19. | R' = CO–C₆H₄–CH₂Br | 11.5 ± 1.5 | 6.9 | — |
| 20b. | R' = CO(CH)₂CO—O—N(COCH₂)(COCH₂) | 20.0 ± 4.5 | — | 0(500) |
| 21. | R' = CO(CH)₆CO—O—N(COCH₂)(COCH₂) | 3.69 ± 0.71 | 15.8 | 40(500) |
| 22. | R' = CO(CH₂)₂–SS–(2-pyridyl) | 23.8 ± 3.51 | — | — |
| 23. | R' = CO(CH₂)₃N(COCH=COCH) | 63 | — | — |

[a] against [³H]PIA after "APNEA";
[b] against [¹²⁵I]APNEA (i.e. N⁶-(4-aminophenylethyl)adenosine;
[c] percent inhibition following a one hour incubation with the compound at the concentration given in parentheses (nM) and washout, in rat brain membranes, against [¹²⁵I]APNEA;
[d] XAC, 8-[4-[[[[(2-aminoethyl)amino]carbonyl]methyl]oxy]phenyl]-1,3-dipropylxanthine The compounds based on N⁶-substituted adenosine are shown in Table II.

TABLE II

Adenosine Derivatives

Structure:

Core structure: adenosine with N6-substituent = HN—⟨phenyl⟩—CH₂CO—R''

| Compound | R'' | Ki at central A1 receptors (nM)[b] rat[a] | calf[b] | % inhib(conc)[c] |
|---|---|---|---|---|
| 24. | R'' = —O—N(COCH₂)(COCH₂) (succinimidyl ester) | 8.37 ± 0.73 | — | — |
| 25. | R'' = —NH—⟨C₆H₄⟩—CH₂CO—O—N(COCH₂)(COCH₂) | 9.60 ± 1.44 | — | — |
| 26a.[d] | R'' = —NH—⟨C₆H₄⟩—CH₂CONH(CH₂)₂NH₂ | 1.3 ± 0.3 | 0.2 | — |
| 26b. | R'' = —NH—⟨C₆H₄⟩—CH₂CONH(CH₂)₂NCS | 4 | 2.5 | — |

For compounds 27–35: R'' = —NH—⟨C₆H₄⟩—CH₂CONH(CH₂)₂NHCSNH—⟨C₆H₄—Y⟩

| Compound | Y | rat[a] | calf[b] | % inhib(conc)[c] |
|---|---|---|---|---|
| 27. | Y = 4-NCS | 0.47 ± 0.13 | 0.1 | >80(50) |
| 28. | Y = 3-NCS | 0.86 | 0.1 | >80(50) |
| 29. | Y = 4-CH₃ | 3.72 ± 0.44 | — | — |
| 30. | Y = 4-OCH₃ | 5 | — | — |
| 31a. | Y = 4-F | 5 | — | — |
| 31b. | Y = 2-F | 10.7 | — | — |
| 32. | Y = 2,3,4,5,6-F₅ | 1.64 ± 0.47 | — | — |
| 33. | Y = 4-Br | 1.19 ± 0.14 | — | — |
| 34. | Y = 4-NO₂ | 1 | — | — |
| 35. | Y = 4-SO₃Na | 100 | — | — |
| 36. | R'' = —NH—⟨C₆H₄⟩—CH₂CONH(CH₂)₂NHCOCH₂Br | 5 | — | — |

[a] against [³H]PIA;
[b] against [¹²⁵I]APNEA;
[c] percent inhibition following a one hour incubation with the compound at the concentration given in parentheses (nM) and washout, in rat brain membranes, against [¹²⁵I]APNEA;
[d] ADAC, N⁶-[4[[[[4-[[[(2-aminoethyl)amino]carbonyl]methyl]anilino]carbonyl]methyl]phenyl]adenosine.

The compounds of the present invention were synthesized as reported by Jacobson et al, or by acylation or esterification of functionalized congeners using readily available crosslinking reagents.

The DITC-XAC shown in FIG. 1 was prepared through acylation of a xanthine amine congener (Jacobson et al. *Proc. Natl. Acad. Sci. USA*, 83: 4089, 1986) in the presence of a large molar excess of the homobifunctional crosslinking reagent 1,4-phenylenediisothiocyanate (DITC). DITC has been used previously for crosslinking of the myosin subfragment 1 (Wells et al., *J. Biol. Chem.*, 255:11135-11140, 1980), crosslinking proteins and phosphatidyl ethanolamine in membranes, *Biochem.* 24: 1403–40, 1985), attaching peptides to resins for stepwise degradations as shown by Horn et al., *FEBS Letters* 21: 67–60, 1972), and as an antihelminthic agent ( Kellner et al., *Nucl. Med., Suppl.* pp. 459–462 and Heptner, *Nucl. Med. Suppl.*, pp 463–465, 1968). Thus, DITC-XAC is related to a class of potent and moderately A₁-selective adenosine antagonists derived from XAC. XAC has been characterized in the cardiovascular and renal systems and as a tritiated radioligand.

The variations of p-DITC-XAC, containing additional spacer groups, e.g. 15e (p-ainophenylacetyl) and 16c (glycyl), were prepared. In each case the final synthetic step (Scheme 1) consisted of treatment of an amine-functionalized xanthine with excess p-DITC. A precursor of 15e, t-butyloxycarbonyl-p-aminophenylacetic acid (Boc-PAPA), 15a, was first converted to the N-hydroxysuccinimide ester, 15b, which reacted with XAC.

with the putative irreversible ligand, followed by a twelve hour washout procedure, which was shown to be not detrimental to the specific binding to adenosine receptors in control membranes. In bovine brain membranes, at a concentration of 500 nM (which is roughly 20-fold greater than the $K_i$ value in the same preparation), 90% of adenosine receptor binding sites, as defined by [$^3$H]XAC binding, were irreversibly inhibited during a one hour incubation. In rat brain at the same

Scheme 1.

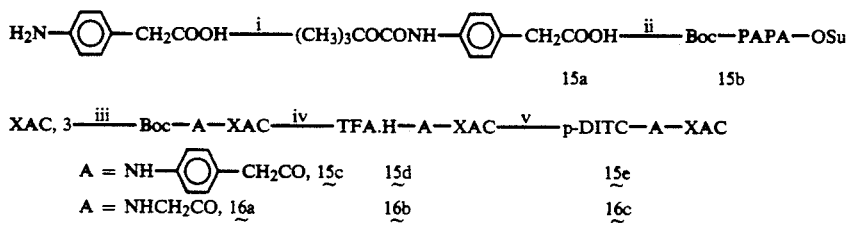

reagents:
i. di-t-butyl dicarbonate;
ii. EDAC, N-hydroxysuccinimide;
iii. either Boc—Gly—OH/EDAC/HOBt (for 16a) or 15b (for 15c);
iv. trifluoroacetic acid;
v. 1,4-pheneylene diisothiocyanate.

As shown in the tables above, the compounds have been assayed for affinity at $A_1$-adenosine receptors in rat brain membranes, using [$^3$H]N$^6$-phenylisopropyladenosine as a radioligand, and were found to have high affinity for this class of receptors. The affinity of compounds 1–36 for $A_1$-adenosine receptors in bovine brain is likely to be greater than in the rat brain, by analogy with other derivatives of N$^6$-phenyladenosine and 1,3-dialkyl-8-phenylxanthine, cf. Ukena et al., FEBS Letters 209;122, 1986.

The compounds, at concentrations relative to the $K_i$-values obtained, were screened for the ability to inhibit competitive binding of the radioligands [$^3$H]PIA to rat brain membranes and [$^3$H]XAC to bovine brain membranes, a shown in Table 1. The m-DITC-XAC, 5b was more than twice as potent in the binding assay than 4b, the para isomer.

We have identified isothiocyanate derivatives of 1,3-dialkyklxanthines (compounds 4b, 5b, and 16c) and of adenosine (compounds 27 and 28), which behave pharmacologically as irreversible inhibitors of central $A_1$-adenosine receptors. p- and m-DITC-XAC are expected to be selective for $A_1$ receptors, based on the characteristics of XAC and its derivatives. The position of the phenylisothiocyanate group made a substantial difference in the potency of inhibition for the xanthine series, with the meta-position favored (5b) over the para-position (4b), but not in the adenosine series. Lengthening the chain between the xanthine pharmacophore and the electrophilic group did not increase inhibitory potency.

In a series of amine-reactive N-hydroxysuccinimide esters (1, 20b, and 21), only the longest of the series, SUS-XAC, 21, inhibits binding irreversibly. This is likely due to the relative geometry of the nucleophilic group relative to the xanthine binding site.

Figure 2:
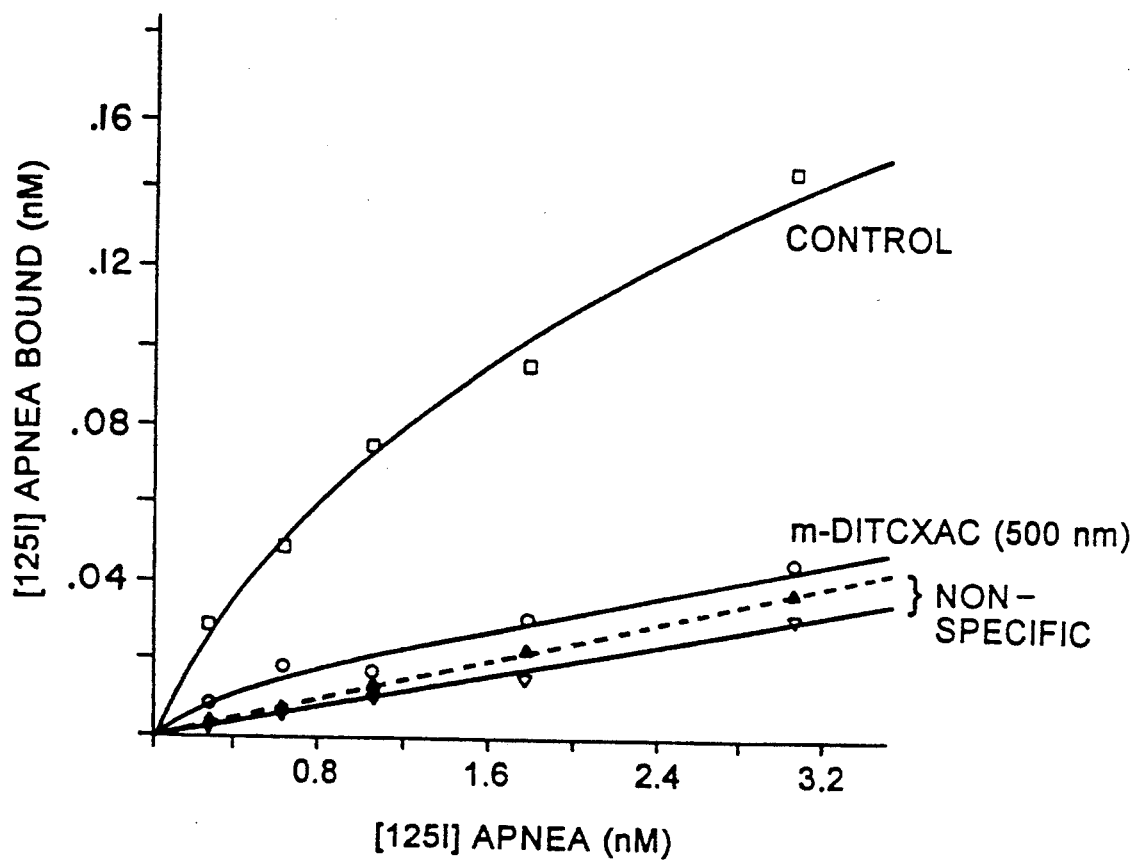
FIG. 2 shows the irreversible inhibition of binding of an adenosine agonist to $A_1$ receptors by a xanthine isocyanate (compound 5b).

Compound 4b, DITC-XAC, the para-isomer, which is distinct from m-DITC-XAC, the meta-isomer, compound 5b, irreversibly inhibits $A_1$-adenosine receptors in membranes form calf brain and from rat brain in a dose-dependent manner. The degree of irreversible binding was determined after a one hour incubation concentration, in three separate experiments, the degree of irreversible activation of $A_2$-adenosine receptors was between 62% and 69%. The degree of inactivation of $A_1$-adenosine receptors by p-DITC-XAC, 4b, was concentration dependent for both bovine and rat brain, as shown in FIG. 2. In five separate experiments, the remaining receptor binding sites after treatment with p-DITC-XAC at $10^{-7}$M (34% of initial density) displayed the same affinity for the radioligand as native receptors ($K_D$-value of 0.5 nM for [$^{125}$I] APNEA i.e., thus the apparent loss of sites is not simply from a partial denaturation of the entire population of receptors. When potent but non-chemically reactive ligands such as XAC were used for comparison, the degree of recovery of [$^{125}$I]APNEA binding sites was 90%, which is nearly total.

Blocking experiments, in which compound 4 was chemically inactivated prior to receptor binding, were also conducted. DITC-XAC, compound 4b, was dissolved in a minimum of dimethylformamide and treated with a ten-fold excess of ethylenediamine. The p-DITC-XAC was shown by thin layer chromatography to be converted totally to the ethylene diamine adduct under these conditions. The $K_i$-values against binding of [$^3$H]XAC to rat brain membranes for p-DITC-XAC and the ethylene diamine adduct were 22 nM and 18 nM, respectively. Although close in affinity to p-DITC-XAC, the ethylene diamine adduct displayed totally reversible binding to $A_2$-adenosine receptors in rat brain.

Covalent labeling of $A_1$-adenosine receptors by compound 4b was demonstrated unequivocally using a high specific activity (approximately 150 Ci/mmol) tritiated preparation of 4b, synthesized from tritiated (on the propyl groups) XAC, 3. An SDS electrophoresis gel separated proteins from a solubilized central $A_1$ receptor preparation, pretreated with compound 4b (lane 1). Specific labeling of the receptor (MW approximately 40,000) was seen upon comparison with the identical experiment containing a high concentration of non-radioactive R-PIA (lane 2), which blocks the irreversible ligand.

p-DITC-XAC is expected to be selective for $A_1$ receptors, based on the characteristics of XAC and its derivatives.

The synthesis of compounds 2b, 18, and 19 was described in Jacobson et al., *Biochem. Pharmacol.*, Vol. 37, No. 19, pp. 3653-3661 1988, hereby incorporated by reference. Compound 18 is synthesized by acylation of the appropriate xanthine using anhydride and compound 19 is synthesized by reacting XAC with the appropriate acid and carbodiimide. Disuccinimidyl tartrate (DTT), disuccinimidyl suberate (DSS), and m-maleimidobenzoyl-N-hydroxysuccinimide ester (MBS) and other homo- and heterobifunctional reagents, which were the immediate precursors from which compounds were prepared, were purchased from Pierce Chemical Co., Rockford, Ill. XCC (8-(4-carboxymethyloxy)phenyl-1,3-dipropylxanthine), the ethyl ester of XCC, and XAC (8-(2-aminoethylaminocarbocyl(4-methyloxy)phenyl-1,3-dipropylxanthine) were synthesized as described in Jacobson et al., *Proc. Natl. Acad. Sci. USA* 83: 4089, 1986. Compounds 27-36 were synthesized by acylation of ADAC, as described in Jacobson et al., *J. Med. Chem.* 28:1341, 1985.

Compounds 26b and 36 were characterized by plasma desportion mass spectroscopy. Positive ion peaks were observed at m+23.

Preparation of 1,3-phenyldiisothiocyanate (m-DITC), Compound 5a

A modification of the procedure of Newman et al., *J. Med. Chem.* 30: 1901, 1987, was used. In this procedure, 1,3-phenylenediamine, 0.211 grams, 1.95 mmol, was dissolved in 80 ml chloroform. Thirty ml water and 0.38 gram, 4.5 mmol, sodium bicarbonate was added, and the mixture was stirred vigorously. After ten minutes, 0.4 ml, 5.2 mmol of freshly distilled thiophosgene was added. After one hour, the phases were separated, and the organic layer was dried over sodium sulfate and evaporated. The residue was triturated with ether:petroleum ether, 1:1, and filtered. The filtrate was evaporated, leaving the product as a white solid (0.30 g, 81% yield), melting at 50.5°-51° C. The NMR spectrum was consistent with the assigned structure. m-DITC was stable to storage at room temperature for at least several weeks.

Preparation of XCC-OSc, compound 1

XCC (45 mg, 0.12 mmol), 37 mg, 0.32 mmol N-hydroxysuccinimide, and 64 mg, 0.32 mmol EDAC were combined in 2 ml DMF. After stirring for five minutes, a solution formed. the solution was cooled in an ice bath, and cold water was added. The resulting precipitate was collected and dried in vacuo. The yield was 48 mg, 86%.

Preparation of XCC-NHCH$_2$CHO, compound 2b

XCC (1.37 g, 3.6 mmol) was condensed with 0.39 ml, 3.6 mmol) aminoacetaldehyde dimethylacetal, purchased from Aldrich, using 0.9 g, 4.4 mmol dicyclhexylcarbodiimide in the presence of 0.4 g, 3 mmol 1-hydroxybenzotriazole. The resulting solid was treated with aqueous trifluoroacetic acid. The product was 8-[2-[formylmethyl[amino[carbonyl[methyl[4-oxyphenyl]]]]]-1,3-dipropylxanthine.

Preparation of DITC-XAC, compound 4b

Fifty mg, 0.26 mmol, of 1,4-phenylenediisothiocyanate, purchased from Fluka Chemical Corp, was dissolved in 3 ml dimethylformamide in a glass container. XAC, 3, 25 mg. 58 micromol, was added in portions with stirring. After one hour, a solution had formed. Ten ml of dry ether and 10 ml petroleum ether were added, followed by scratching with a glass rod. After several hours, a precipitate formed. The solid was filtered, washed with ether, and dried in vacuo, providing 20 mg, 56% yield, of product, 1,3-dipropyl-8-(4-(isothiocyanotophenyl)aminothiocarbonyl(2-aminoethylaminocarbonyl(4-methoxy(phenyl)))xanthine. The solid decomposes at 140° C., forming another solid which then melts at 220° C. NMR spectrum in DMSO D6 δ9.79 (NH), 8.31 (t, 1H, NH), 8.07 (d, 2H, 8-Ar, C-2 and C-6, J=8.8 Hz), 7.95 (1H, NH), 7.50 (d, 2H, NH-Ar, C-3 and C-5, J=8.8 Hz), 7.33 (d, 2H, NH-Ar, C-2 and C-6, J=8.7 Hz), 7.10 (d, 2H, 8-AR, C-3 and C-5, J=8.8 Hz), 4.57 (s, 2H, CH$_2$O), 4.02 and 3.87 (each t, C-1, Pr, J=?Hz), 3.62 (m, 2H, C-2 Et), 3.4 (2H, C-1 Et), 1.74 and 1.58 (each m, 2H, C-2 Pr), 0.89 (q, 6H, C-3 Pr).

p-DITC-XAC was shown by thin layer chromatography (silica, chloroform:methanol:acetic acid, 85:10:5) to be quantitatively reactive towards primary amines, such as ethylene diamine in molar excess, for which were obtained Rf values of 0.87 and 0.33 for DITC-XAC and product, respectively. DITC-XAC is stable to storage at −20° C.

Preparation of Bromoacetyl-XAC, compound 8

XAC, 0.13 g, 0.30 mmol, was suspended in 4 ml dimethylformamide and treated with 90 mg bromoacetic anhydride. N-methylmorpholine, 30 microliters, 0.29 mmol, was added slowly. The product, 8-[2-[4-bromoacetylaminoethyl[amino[carbonyl[methyloxyphenyl]]]]-1,3-dipropylxanthine, was isolated in 57% yield.

Preparation of SUS-XAC, compound 21

XAC was suspended in DMF and treated with 1.5 equivalents of disuccinimidyl suberate. After one hour, the product was isolated as a precipitate in 30% yield upon addition of ether and petroleum ether.

Preparation of epsilon -(p-Bromoethylbenzoyl)-D-lysyl-XAC trifluoroacetate

Alpha-(t-butyloxycarbonyl)-epsilon-(benzyloxycarbonyl)-D-lysyl-XAC was hydrogenated over palladium black in dimethylformamide. The pure product, alpha-(t-butyloxycarbonyl)-D-lysyl-XAC was isolated by ether precipitation in 54% yield and was coupled to alpha-bromotoluic acid using the EDAC/HOBt procedure. The product was isolated by addition of water in 82% yield and treated with trifluoroacetic acid at room temperature for ten minutes. the acid was evaporated, and the residue was recrystallized from methanol/ether to give the title compound in 62% yield.

Preparation of ADAC-NCS, compound 26b

ADAC, 25 mg, 43 micromol, and 6 microliters triethylamine were dissolved in 1 ml dimethylformamide with warming. After cooling in an ice bath, 3.9 microl, 51 micromol of distilled thiophosgene was added with stirring. Water and saturated sodium chloride were added to obtain a white precipitate, which was dried in vacuo over sodium hydroxide. The yield was 13 mg, or 48%, of product. IR peaks appeared at 3460, 2120, 1640, 1600, 1515, 1480, 1420, 1100, 1060, and 1030 cm$^{-1}$. Thin layer chromatography and the Cf plasma desorption spectrum was consistent with the assigned structure and showed no evidence of residual ADAC.

For the biochemical assays, stock solutions of xanthines in the millimolar concentration range in dimethylsulfoxide were prepared and stored frozen. The solutions were warmed to 50° C. prior to dilution in aqueous medium. The inhibition of binding of 1 nM [$^3$H]N$^6$-phenylisopropyladenosine to A$_1$ adenosine receptors in rat cerebral cortex membranes was assayed as described in Jacobson et al., *Proc. Nat. Acad. Sci. USA*, 83:4089, 1986. Inhibition of binding by a range of concentrations of a xanthine or adenosine derivative was assessed in triplicate in at least three separate experiments. The IC$_{50}$ values were converted to K$_i$ values using a K$_D$ value for [$^3$H]PIA of 1.0 nM and the Cheng-Prusoff equation.

Table III presents the analytical data for compounds disclosed above.

dues, alpha amino groups, and sulfhydryl groups are known to be present in the primary sequence of other membrane bound receptors, such as beta-adrenergic receptors, in the vicinity of the extracellular binding site. It is possible that there is a free thiol group present on the A$_1$-receptor.

The isothiocyanate group is known to be preferentially reactive towards primary and secondary amino groups and thiol groups. Other isothiocyanate-derivatized ligands have been found to be irreversible inhibitors of binding to receptors, cf. Rafferty et al., *FEBS Letters*, 181: 318-322, 1985. Newman et al., *J. Med. Chem.*, 30:1901, 1987. These probes have found wide application in studying the pharmacology and physiology of opiate and other receptors.

The identification of a chemically-irreversible inhibitor of adenosine receptors leads to studies in a number of physiological systmes. For example, in the kidney both A$_1$ and A$_2$ receptors are present, and these receptors are not readily characterized in competitive binding studies, but might be with an irreversible ligand such as DITC-XAC. The central effect of adenosine,

TABLE III

| compd | method$^a$ | % yield | mp, °C. | formula | anal |
|---|---|---|---|---|---|
| 2a | A | 57 | 238-239 | $C_{23}H_{31}N_5O_6$ | C,H,N |
| 2b | B | 76 | 203-206 | $C_{22}H_{27}N_5O_5$ | |
| 4b | C | 60 | 140d | $C_{29}H_{32}N_8O_4S_2.H_2O$ | C,H,N |
| 5a | D | 81 | 50.5-51 | $C_8H_4N_2S_2$ | C,H,N |
| 5b | C | 62 | 186-188 | $C_{29}H_{32}N_8O_4S_2.0.5H_2O$ | C,H,N |
| 6 | C | 87 | 205-208 | $C_{29}H_{35}N_7O_4S$ | C,H,N |
| 7 | C | 80 | 170-174 | $C_{29}H_{35}N_7O_4S$ | |
| 8 | C | 89 | 163-165 | $C_{28}H_{32}N_7O_4FS$ | |
| 9 | C | 58 | 257-265 | $C_{28}H_{28}N_7O_4F_5S.0.5H_2O$ | C,H,N |
| 10 | C | 70 | 205-208 | $C_{28}H_{32}N_7O_4BrS$ | C,H,N |
| 11 | C | 90 | 248-250 | $C_{28}H_{32}N_8O_6S$ | |
| 12 | C | 64 | 275d | $C_{28}H_{32}N_7O_7S_2Na$ | |
| 13 | E | 20 | 256-260 | $C_{27}H_{31}N_6O_8S_2Cl$ | |
| 14 | E | 90 | 211-216 | $C_{28}H_{34}N_6O_6S.0.5H_2O$ | C,H,N |
| 15a | F | 40 | 141.5-142.5 | $C_{13}H_{17}NO_4$ | C,H,N |
| 15b | A | 69 | 169-170 | $C_{17}H_{20}N_2O_6$ | C,H,N |
| 15c | G | 75 | 215-220 | $C_{34}H_{43}N_7O_7.0.5H_2O$ | C,H,N |
| 15d | B | 89 | | $C_{31}H_{36}N_7O_7F_3$ | |
| 15e | C | 50 | 194-204 | $C_{37}H_{39}N_9O_5S_2$ | |
| 16a | A | 81 | 210-212 | $C_{28}H_{39}N_7O_7.H_2O$ | C,H,N |
| 16b | B | 100 | | $C_{25}H_{32}N_7O_7F_3.CF_3COOH$ | H,N;C* |
| 16c | C | 90 | 173-175 | $C_{31}H_{35}N_9O_5S_2.H_2O$ | C,H;N* |
| 17 | A | 33 | 236-239 | $C_{28}H_{38}N_6O_6$ | C,H,N |
| 18 | F | 93 | 275-279 | $C_{23}H_{29}N_6O_5Br.H_2O$ | C,H,N |
| 19 | G | 78 | 277-280 | $C_{29}H_{33}N_6O_5Br$ | |
| 20a | F | 80 | 210-212 | $C_{25}H_{32}N_6O_7.1.5H_2O$ | C,H,N |
| 20b | A | 83 | 161-162 | $C_{29}H_{35}N_7O_9.H_2O$ | C,H,N |
| 21 | G | 92 | 189-197 | $C_{33}H_{43}N_7O_9S.DMF$ | C,H,N |
| 22 | G | 83 | 212-219 | $C_{29}H_{35}N_7O_5S_2$ | C,H,N |
| 23 | G | 74 | 203-206 | $C_{29}H_{35}N_7O_7.0.5H_2O$ | C,H,N |
| 24 | A | 41 | 132-135 | $C_{22}H_{22}N_6O_6.1.5H_2O$ | C,H,N |
| 26b | D | 48 | | $C_{29}H_{30}N_8O_6S$ | |
| 27 | C | 77 | 179-181 | $C_{36}H_{36}N_{10}O_6S_2.H_2O$ | C,H,N |
| 28 | C | 78 | 182-183 | $C_{36}H_{36}N_{10}O_6S_2$ | C,H,N |
| 29 | C | 90 | 178-182 | $C_{36}H_{39}N_9O_6S.0.5H_2O$ | C,H,N |
| 30 | C | 70 | 171-174 | $C_{36}H_{39}N_9O_7S$ | |
| 31a | C | 91 | 171-174 | $C_{35}H_{36}N_9O_6FS$ | |
| 31b | C | 63 | 169-174 | $C_{35}H_{36}N_9O_6FS.2H_2O.2DMF$ | C,H,N |
| 32 | C | 40 | | $C_{35}H_{32}N_9O_6F_5S.0.5H_2O$ | C,H,N |
| 33 | C | 87 | 178-182 | $C_{35}H_{36}N_9O_6BrS$ | C,H,N |
| 34 | C | 80 | 172-175 | $C_{35}H_{36}N_{10}O_8S$ | |
| 35 | C | 51 | 219-229 | $C_{35}H_{36}N_9O_9S_2Na$ | |
| 36 | F | 62 | d220° | $C_{30}H_{33}N_8O_7Br$ | |

$^a$key to synthetic methods: A - carbodiimide coupling; B - acid cleavage; C - thiourea from amine and isothiocyanate; D - isothiocyanate from amine and thiophosgene; E - sulfonamide from amine and sulfonyl chloride; F - acylation of amine; G - amide from amine and N-hydroxysuccinimide ester.

The choice of chain lengths and reactive electrophilic groups present in compounds 1-18 is for determination of which nucleophilic group of the adenosine receptor protein participates in the inhibition reaction and to probe the architecture of the binding site. Lysyl residues evidenced in locomotor depression, have not been ascribed clearly to either A$_1$ or A$_2$ receptor subtypes. The addition of DITC-XAC as a specific inhibitor in an isolated organic preparation of in vivo may prove to be a powerful tool for the study of regulatory effects of endogenous adenosine and delineation of the role and $A_1$ and $A_2$ receptor subtypes.

The irreversible inhibitors of adenosine receptors can be used therapeutically. In peripheral sites, a long acting adenosine antagonist, by virtue of covalent bond formation with receptor, can be used as a diuretic or kidney-protective agent, cardiotonic, or stimulator of the immune system. An irreversible adenosine agonist is useful as a vasodilator, an anti-diuretic agent, or an immunosuppressant.

The preferred dosages of the compounds of the present invention are within the skill of the art, based upon the effects to be achieved with the compound as well as the size and the physical condition of the patient. Generally, a dosage sufficient to achieve a plasma level of from about 1 to 25 micrograms/ml of active ingredient is sufficient to provide effective treatment of the condition sought to be treated.

The compounds of the present invention can be administered in an initial loading dose of from 1-10 mg/kg followed by a maintenance dose, which may be administered continuously, of from about 0/50 to 1.50 mg/kg/hour.

Administration of these amounts is sufficient for achieving and maintaining a plasma level as indicated above for any method in which the compounds or their pharmaceutically effective derivatives are absorbed into the blood stream without being absorbed. Examples, not intended to be limiting, include intravenous injection, absorption by the small intestine from capsules that release the active ingredients, absorption by the large intestine from suppositories, absorption by the small intestine from enteric coated capsules or tablets, or absorption through the lungs. Methods that require the compounds to pass through the stomach may be subject to the destruction of an agonist and accordingly must be either protected in a form that is not destroyed in the stomach or administered in a sufficiently large dose so that the amount reaching the blood stream is sufficient to achieve the desired effective level.

The compounds of the present invention may be admixed with any pharmaceutically acceptable carrier or carriers, such as water, ethanol, inert solids, or any other carrier customarily used for the type of administration in question.

While the invention is described above in relation to certain specific embodiments, it will be understood that many variations are possible, and that alternative materials and reagents can be used without departing from the invention. In some cases such variations and substitutions may require some experimentation, but such will only involve routine testing.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. 8-aryl-substituted xanthine ligand compounds selected from the group consisting of

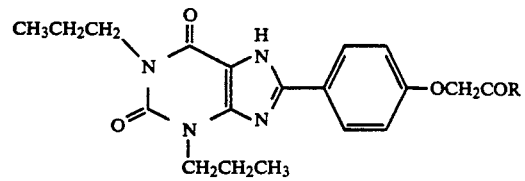

wherein R is selected from the group consisting of —NHCH$_2$CHO and —NH(CH$_2$)$_2$NHR', wherein R' is selected from the group consisting of

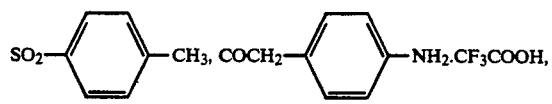

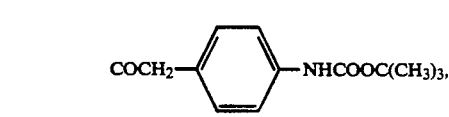

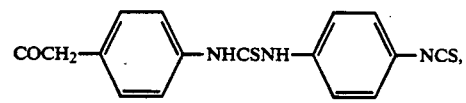

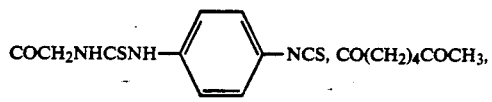

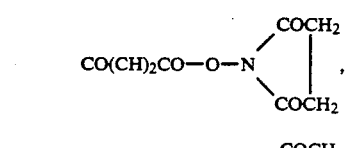

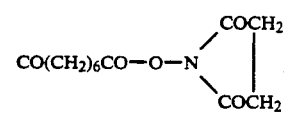

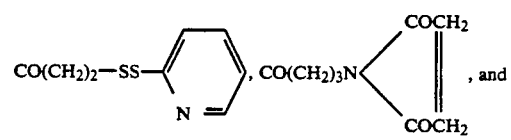

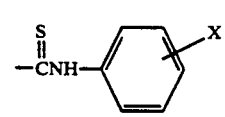

wherein X is selected from the group consisting of NCS, CH$_3$, OCH$_3$, F$_n$, Br, NO$_2$, SO$_3$Na wherein n is an integer of from 1 to 5.

2. The compound of claim 1 wherein R' is

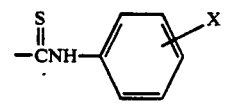

and X is NCS.

3. A composition comprising an 8-aryl-substituted xanthine according to claim 1 and a pharmaceutically acceptable carrier.

4. A method of stimulating the immune system in a host comprising administering to said host an effective amount of an 8-aryl-substituted xanthine according to claim 1.

5. A method of inducing diuresis in a host comprising administering to said host an effective amount of an 8-aryl-substituted xanthine according to claim 1.

6. A method of regulating the action of the heart in a host comprising administering to said host an effective amount of an 8-aryl-substituted xanthine according to claim 1.

7. The ligand of claim 1, wherein R is —NHCH₂CHO.

8. The ligand of claim 1, wherein R is

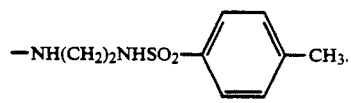

9. The ligand of claim 1, wherein R is

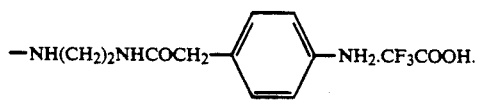

10. The ligand of claim 1, wherein R is

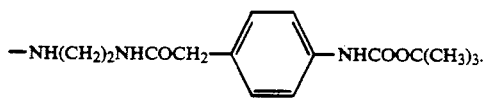

11. The ligand of claim 1, wherein R is

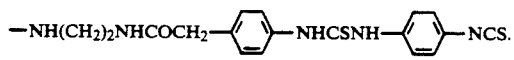

12. The ligand of claim 1, wherein R is

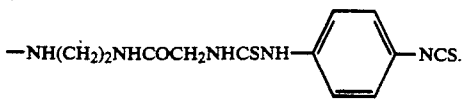

13. The ligand of claim 1, wherein R is —NH(CH₂)₂NHCO(CH₂)₄COCH₃.

14. The ligand of claim 1, wherein R is

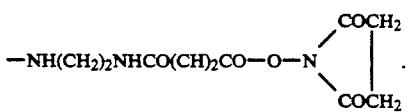

15. The ligand of claim 1, wherein R is

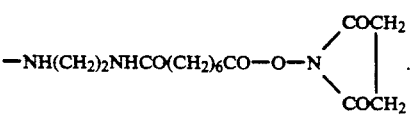

16. The ligand of claim 1, wherein R is

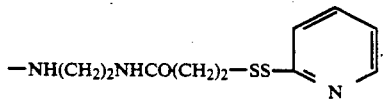

17. The ligand of claim 1, wherein R is

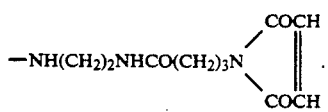

18. The ligand of claim 1, wherein R is

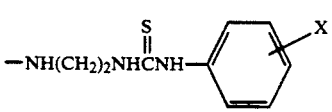

wherein X is selected from the group consisting of: NCS, CH₃, OCH₃, F$_n$, Br, NO₂, SO₃Na wherein n is an integer of from 1 to 5.

* * * * *